United States Patent
Springhorn et al.

(10) Patent No.: US 6,911,140 B2
(45) Date of Patent: Jun. 28, 2005

(54) GAS SENSOR ELEMENT AND METHOD FOR DETERMINING THE CONCENTRATION OF A GAS COMPONENT IN A GAS MIXTURE

(75) Inventors: Carsten Springhorn, Stuttgart (DE); Bernhard Bloemer, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 411 days.

(21) Appl. No.: 09/969,265

(22) Filed: Oct. 1, 2001

(65) Prior Publication Data

US 2002/0078743 A1 Jun. 27, 2002

(30) Foreign Application Priority Data

Sep. 29, 2000 (DE) .......................................... 100 48 240

(51) Int. Cl.[7] .............................................. G01N 27/41
(52) U.S. Cl. ........................ 205/781; 205/784; 204/425
(58) Field of Search ................................ 204/424, 425, 204/426, 427; 205/781, 783.5, 784, 789.5; 73/23.31

(56) References Cited

U.S. PATENT DOCUMENTS

| | | | | |
|---|---|---|---|---|
| 4,496,433 A | * | 1/1985 | Annino et al. | ............... 205/784 |
| 4,622,125 A | * | 11/1986 | Oyama et al. | ............... 204/406 |
| 6,051,123 A | * | 4/2000 | Joshi et al. | .................. 204/424 |

FOREIGN PATENT DOCUMENTS

| EP | 0 678 740 A1 | * | 10/1995 |
|---|---|---|---|
| EP | 0 924 514 A2 | * | 6/1999 |

OTHER PUBLICATIONS

F. Ménil et al., Sensors and Actuators B, 67 (2000), pp. 1 to 23.

\* cited by examiner

*Primary Examiner*—Kaj Olsen
(74) *Attorney, Agent, or Firm*—Kenyon & Kenyon

(57) ABSTRACT

A sensor element and a method for determining the concentration of at least one gas component, especially of a nitrogen oxide, in a gas, mixture. For this purpose, the sensor element includes at least one first electrode exposed to the gas component to be analyzed and at least one reference electrode, which are electrically interconnected by a first solid electrolyte. Furthermore, an electric current between the first electrode and a further electrode is measured continuously or in sampling fashion in response to the application, especially the setting, of an electric voltage between first electrode and the reference electrode due to a chemical reaction proceeding at the first electrode, by which the concentration of the gas component to be analyzed in the gas mixture can be determined. During this process, the application or setting of the electric voltage takes place only during recurring time intervals. In addition, the electric current between the first electrode and the further electrode is measured at least intermittently within the recurring time intervals.

16 Claims, 1 Drawing Sheet

GAS SENSOR ELEMENT AND METHOD FOR DETERMINING THE CONCENTRATION OF A GAS COMPONENT IN A GAS MIXTURE

FIELD OF THE INVENTION

The present invention relates to a gas sensor element and a method for determining the concentration of a gas component in a gas mixture, especially of nitrogen oxides.

BACKGROUND INFORMATION

There are believed to be various gas sensors, as used for analysis of the exhaust gases of internal combustion engines and, among other things, also for the analysis or detecting the presence of nitrogen oxides ($NO_x$). A survey may be found in F. Ménil et al., Sensors and Actuators B, 67 (2000), pages 1 to 23. A gas sensor for detecting nitrogen oxides is also discussed in European Patent Application No. 0 678 740, and apparently works on the principle of a limiting current sensor and has a double chamber arrangement, in which chambers are separated from each other by a diffusion barrier.

In such a limiting current sensor, the limiting currents, which appear at a typical concentration of nitrogen oxides in an exhaust gas of an internal combustion engine of 500 ppm, lie around ca. 7 $\mu A$, so that they can be processed further, and used as control or regulating quantities only with difficulty by customary motor vehicle electronic systems.

The functioning of limiting current sensors is based on applying a constant voltage between two electrodes separated from each other by a solid electrolyte, or, in the case of a three-electrode configuration, setting it by using a potentiostat. This voltage leads to an electrical current between two electrodes which is based on electrochemical conversion of gas components, or rather exhaust gas components.

SUMMARY OF THE INVENTION

A suitable geometry of the electrodes or the sensor may be used so that this current, as limiting current, may essentially no longer depend on the applied or set voltage, but only on the restricted inflow of the relevant gas components to the respective electrode caused by the geometry of the sensor. This limiting current, then, represents the signal of the sensor.

Starting from a limiting current sensor, an object of an exemplary embodiment of the present invention is to make available a gas sensor whose current signal is greater than the measurable signals of customary limiting current sensors. However, besides that, the various gas components, especially the nitrogen oxide proportion, were to be determinable as before from this current signal.

The sensor element, according to an exemplary embodiment of the present invention, for determining the concentration of a gas component, and the exemplary method according to the present invention is believed to have the advantage, compared to the related art, that, by using a modified ascertainment, as compared to known limiting current sensors, of the occurring electrical currents, the measured electrical currents, or rather the sensor signal received, in the sensor element are appreciably greater, and can thereby be more easily evaluated and processed further than could be done up to the present.

In particular, the limiting current of the sensor element is not evaluated by the ascertainment of the signal on which the present invention is based, but instead, using a voltage source during recurrent, especially periodic time intervals of suitable length, a voltage is applied, or potentiostatically set, for example, which would lead to a limiting current after a short time of typically a few milliseconds. However, until the limiting current is reached, the initially measurable electric current is greater than the limiting current, and thus can instead be advantageously used for determining the concentration.

It is also believed to be advantageous that, outside the recurring time intervals, the voltage source, or the potentiostat encompassing it, as the case may be, is electrically separate from the sensor element or each electrode or reference electrode, so that no current flows at this time, and also no exhaust components, that are relevant or rather to be analyzed, are converted in the sensor element. Thus, during such pause intervals, the gas components to be analyzed can collect above the respective electrode at which the chemical reaction is taking place which causes the electrical current.

This enrichment may advantageously proceed until the gas component to be analyzed is present above this electrode in the same concentration as outside the sensor element, i.e. as in the exhaust gas. During the subsequent time interval the exhaust gas components to be analyzed are then electrochemically converted or reduced above the electrode, by the action of the reconnected voltage source or potentiostat, as the case may be, and the electrical current brought about thereby.

Furthermore, the electrical current flowing during the recurring time intervals can also be advantageously, additionally or alternatively integrated by an integrator circuit generally known in electrotechnology, so that the current integral thus ascertained can be evaluated in addition to, or instead of the electrical current which has already been increased compared to customary, limiting currents. In particular, such an integration leads to a further signal amplification.

Thus, it may be especially advantageous if at, or in the surroundings of that electrode, which is used for the electrochemical conversion of the gas components to be analyzed, an additional apparatus, arrangement or structure of storage is provided, which absorbs or stores the gas components to be analyzed outside the recurring time intervals, and yields them up again during the recurring time intervals in which the electrochemical conversion takes place. This should lead to a further amplified electrical current, and the signal obtained by integration should also be increased.

A layer applied on the electrode may be especially suitable as a storage apparatus, arrangement or structure, or a material integrated into the electrode, such as a mixture of barium oxide, barium carbonate and cerium oxide, such as is also used in customary $NO_x$ storage catalysts.

Alternatively, it can also be provided that the storage apparatus, arrangement or structure is not directly in contact with the electrode but is only positioned in the surroundings of the electrode.

A time duration of 1 ms to 100 ms is believed to be especially advantageous as the length of the recurring time intervals, which may recur periodically.

Between the recurring time intervals there may advantageously be pause intervals with a length of 1 ms to 100 ms.

Finally, the amplitude of the applied electrical voltage is believed to advantageously be between 0.5 volt and 1.5 volt, particularly 1 volt.

As compared to a customary limiting current sensor, at a concentration of nitrogen oxides in an exhaust gas of an internal combustion engine of 500 ppm, currents of 15 $\mu A$ are measurable in the manner explained, which, by integration or the storage apparatus, arrangement or structure commented upon, can be increased with no further problem.

DETAILED DESCRIPTION

Figure 1:
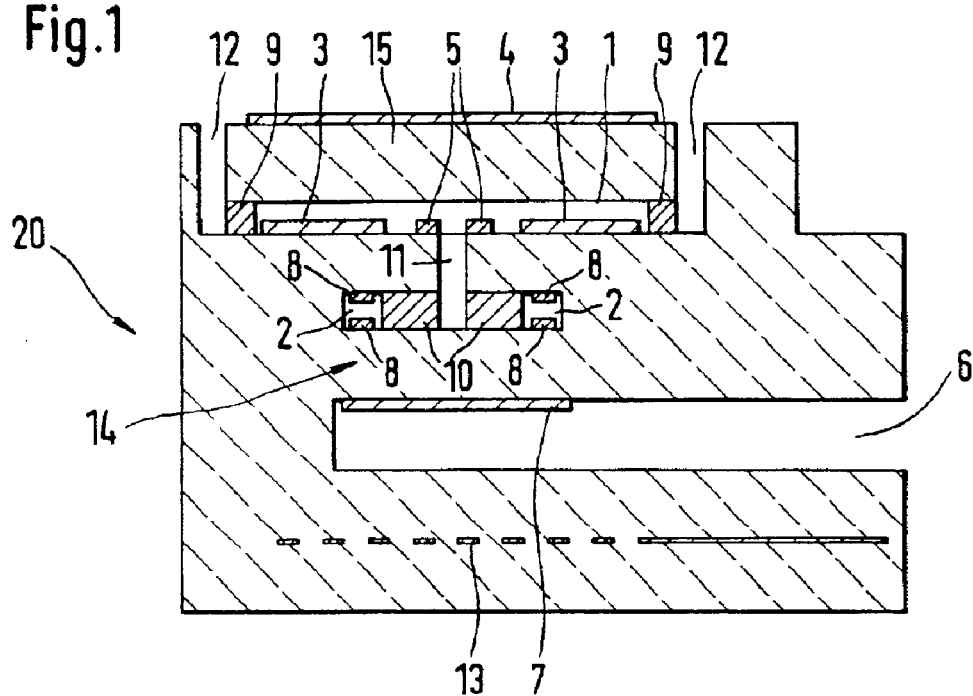
FIG. 1 shows an $NO_x$ double chamber gas sensor as the first exemplary embodiment, in cross section.

FIG. 1 may start from a double chamber gas sensor for detecting nitrogen oxides, as discussed with respect to that of European Patent Application No. 0 678 740.

Specifically, the gas sensor as in FIG. 1 has a sensor element 20 having an oxygen ion-conducting ceramic as solid electrolyte, produced by thick film technology. The sensor element has two chambers, a first chamber 1 and a second chamber 2, positioned one behind the other. In particular, the second chamber 2 is post-connected to chamber 1 but, at the same time, is connected with it in a gas-permeable fashion.

It is further provided that the first chamber 1 has a second electrode 3, which is used in combination with a counter-electrode 4 for electrochemical pumping off of oxygen contained in the exhaust gas that is present. Second electrode 3 and counterelectrode 4 are separated from each other by a second oxygen ion-conducting solid electrolyte 15 for this purpose.

Access to first chamber 1 of the exhaust gas present on the outside takes place via borings 12, from which first chamber 1 is separated by first diffusion barriers 9. Thus the oxygen contained in the exhaust gas is pumped out of first chamber 1, that is, a pump cell is realized, a developing pumping flow being regulated with the aid of a measuring electrode 5, sensitive to oxygen, and a reference electrode 7, in contact with a reference gas via a reference gas channel (air, in the exemplary embodiment being explained) so that a constant voltage is set between measuring electrode 5 and reference electrode 7. This constant voltage is a measure of oxygen concentration in first chamber 1 set as low as possible.

In this connection, it is further important that, for the purpose of detecting nitrogen oxides in second chamber 2, the material of second electrode 3 is chosen so that in first chamber 1 or at second electrode 3, respectively, no nitrogen oxide is pumped off together with oxygen.

As seen in FIG. 1, from first chamber 1 an access passage 11, in the form of a boring leads to second chamber 2, in which there are two oppositely facing, ring-shaped first electrodes 8. Furthermore, between access passage 11 and first electrodes 8 a second diffusion barrier 10 is positioned. Besides that, it is provided that first electrodes 8 are connected, via an oxygen ion-conducting first solid electrolyte 14 separately from reference electrode 7, to the latter via an electrical circuit explained below. The electrode material of first electrode 8 in second chamber 2 is selected in a known way, such that a catalytic decomposition of $NO_x$ (nitrogen oxides) to oxygen ($O_2$) and nitrogen ($N_2$) can take place. The oxygen developing from this process is then pumped off electrochemically with the aid of an electrical voltage that is applied between first electrodes 8 and reference electrode 7 or is set potentiostatically, as long as this voltage between first electrodes 8 and reference electrode 7 is present.

In addition it is provided that sensor element 20 can be heated by a heating element 13 in any suitably appropriate way.

As to further details of sensor element 20, they may be from European Patent Application No. 0 678 740.

As opposed to a "usual" limiting current sensor, it is further provided that an electric voltage is applied or set, with the aid of the electrical circuit provided between first electrodes 8 and reference electrode 7, only temporarily during recurring time intervals, so that only during these time intervals an electrochemical conversion from nitrogen oxides to oxygen and nitrogen takes place at first electrodes 8, and also only during these time intervals an electric current is measurable between first electrodes 8 and reference electrode 7 through first solid electrolyte 14.

A suitably appropriate electric circuit, which is not shown in FIG. 1, but which is believed to be available to one skilled in the art, has a voltage source for generating a specific, predefined electric voltage which is constant each time during the recurring time intervals.

The length of the recurring time intervals is selected so that, during the time intervals, the electric current, measurable as a function of time, between first electrodes 8 and reference electrode 7 is greater than a limiting current, measurable at a corresponding, timewise constant electric voltage.

Outside the recurring time intervals, the electric voltage is applied or set via the electrical circuit and has a lower value than inside the recurring time intervals or is at least nearly zero, or the voltage source is electrically separated from first electrodes 8.

The electric circuit not illustrated in FIG. 1 further contains a "customary" current measuring device for the pointwise or continuous measuring of the current appearing between first electrodes 8 and reference electrode 7 during the recurring time intervals. This electric current is a function of the concentration of the gas components to be analyzed in second chamber 2, and thereby also of the concentration of these gas components in the exhaust gas to be analyzed.

In the exemplary embodiment, the length of the periodically recurring time intervals is 50 ms. The pause intervals lying between the time intervals likewise have a duration of 50 ms.

In another exemplary embodiment, the described electrical circuit additionally has a "usual" integrator circuit which is used for recording the integral of the electric current flowing between first electrodes 8 and reference electrode 7 during the recurring time intervals. In particular, the integral of the flowing electric current is formed using this integrator circuit during a measuring interval lying within the recurring time interval or coinciding with it. This integral can be used instead of, or besides the electrical current ascertained by a sort of sampling during the corresponding time interval for determining the concentration of the gas components to be analyzed, since it is proportional to it.

In another exemplary embodiment, it is provided that into first electrodes 8 a material is integrated which is suitable for storing nitrogen oxides. Such a material may be, for example, a mixture of barium oxide, barium carbonate and cerium oxide.

Besides integrating these materials into first electrodes 8, one can also apply a porous coating to electrodes 8 using a layer of such a material, or storage of nitrogen oxides made of this material can be positioned in the vicinity of first electrodes 8. This storage of nitrogen oxide is used for enriching the gas components to be analyzed in each case, outside the recurring time intervals, so that during the recurring time intervals a greater quantity of nitrogen oxide is available at first electrodes 8, which, in turn, increases the electric current appearing between first electrodes 8 and reference electrode 7.

Figure 2:
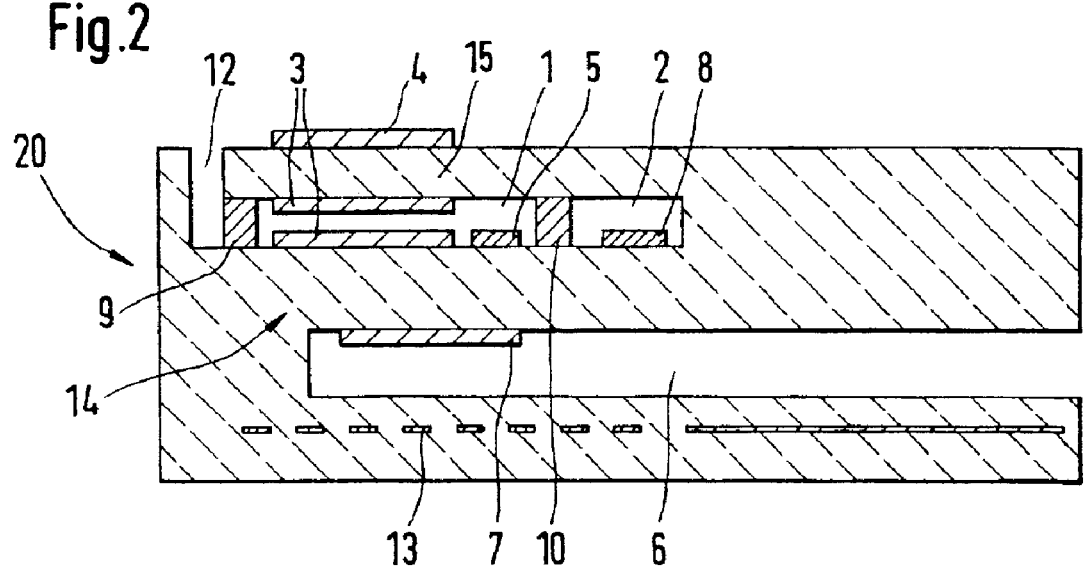
FIG. 2 illustrates a second exemplary embodiment of an $NO_x$ double chamber gas sensor in cross section, modified compared to FIG. 1.

FIG. 2 shows an exemplary embodiment alternative to FIG. 1, the same components, or rather components having the same function being denoted by the same reference numeral.

Specifically, it is also provided according to FIG. 2 that first electrode 8 and reference electrode 7 are in contact with the electrical circuit already explained in connection with FIG. 1, or are interconnected with it, so that between first electrode 8 and reference electrode 7 an electric voltage is set only during the recurring time intervals, and only during these recurring time intervals an electric current is measurable between first electrode 8 and reference electrode 7 or counterelectrode 4.

Other than that, the exemplary embodiment of sensor element 20 according to FIG. 2 is completely or essentially analogous to the exemplary embodiment according to FIG. 1, apart from the modified construction and the modified positioning of first chamber 1 or second chamber 2, respectively.

In the exemplary embodiment according to FIG. 2, in particular, the already explained integrator circuit or a storage medium in the region of second chamber 2 can be provided, using which, nitrogen oxide can be temporarily stored outside the recurring time intervals.

What is claimed is:

1. A sensor element for determining a concentration of at least one gas component in a gas mixture, comprising:
   at least one first electrode exposed to the at least one gas component to be analyzed;
   a second arrangement;
   at least one reference electrode electrically interconnected by a first solid electrolyte to the at least one first electrode, wherein the second arrangement is configured to measure an electric current at least one of continuously and non-continuously between the at least one first electrode and one of the at least one reference electrode and a counterelectrode, in response to at least one of the applying and the setting an electric voltage between the at least one first electrode and the at least one reference electrode due to a chemical reaction proceeding at the at least one first electrode, the concentration of the at least one gas component in the gas mixture being determinable from the electric current; and
   a first arrangement configured to at least one of apply and set the electric voltage between the at least one first electrode and the at least one reference electrode only during recurring time intervals;
   wherein the second arrangement is configured to measure the electric current between the at least one first electrode and one of the at least one reference electrode and the counterelectrode, at least intermittently within the recurring time intervals.

2. The sensor element of claim 1, further comprising:
   at least one reference gas channel, wherein the at least one reference gas is applied to the at least one reference electrode via the at least one reference gas channel.

3. The sensor element of claim 1, wherein the sensor element includes a first chamber, to which the gas mixture can be applied, that is provided with a second electrode which is connected to the counterelectrode via a second solid electrolyte, and a second chamber, downstream of the first chamber and connected to the first chamber in a gas-permeable manner, in which the at least one first electrode is positioned.

4. The sensor element of claim 3, wherein the first chamber together with the second electrode and the counterelectrode is a pump cell for electrochemically pumping off oxygen from the gas mixture.

5. The sensor element of claim 3, further comprising:
   a first diffusion barrier positioned in the first chamber; and
   a second diffusion barrier positioned in the second chamber;
   wherein the gas mixture at least one of accesses the first chamber via the first diffusion barrier and accesses the second chamber via the second gas diffusion barrier.

6. The sensor element of claim 1, wherein the first arrangement includes an electric circuit and a voltage source for generating at least one of a specific electric voltage and a predefinable electric voltage that is constant during the recurring time intervals.

7. The sensor element of claim 1, wherein the first arrangement is configured to select a length of the recurring time intervals so that the electric current, which is measured as a function of time during the recurring time intervals, between the at least one first electrode and the at least one reference electrode is greater than a limiting current, measured at a constant electric voltage during a corresponding time.

8. The sensor element of claim 1, wherein, outside the recurring time intervals:
   the electric voltage at least one of applied and set by the first arrangement is at least one of smaller than within the recurring time intervals and is at least nearly zero;
   the first arrangement is electrically separated from at least one of the at least one first electrode and the at least one reference electrode outside of the recurring time intervals.

9. The sensor element of claim 1, wherein the second arrangement includes at least one of:
   a current measuring device for one of point-by-point recording and continuous recording of the electric current during the recurring time intervals; and
   an integrator circuit for recording an integral of the electric current, the integrator circuit forming the integral during a measuring interval at least one of lying within a recurring time interval and coinciding with the recurring time interval.

10. The sensor element of claim 1, wherein one of the following is satisfied:
    the at least one first electrode is at least one of supplied with a storage arrangement to store temporarily the at least one gas component to be analyzed; and
    the storage arrangement to store temporarily the at least one gas component to be analyzed is provided in a vicinity of the at least one first electrode.

11. The sensor element of claim 10, wherein the storage arrangement includes one of a layer applied on the at least one first electrode, and a material integrated into the at least one first electrode, the layer and material including at least one of barium oxide, barium carbonate and cerium oxide.

12. The sensor element of claim 10, wherein the storage arrangement enriches the at least one gas component to be analyzed outside of the recurring time intervals.

13. A method for determining a concentration of at least one gas component in a gas mixture using a sensor element that includes at least one first electrode exposed to the at least one gas component to be analyzed, at least one reference electrode electrically interconnected by a first solid electrolyte to the at least one first electrode, comprising:

at least one of applying and setting an electric voltage between the at least one first electrode and the at least one reference electrode only during recurring time intervals due to a chemical reaction proceeding at the at least one first electrode; and measuring an electric current at least one of continuously and non-continuously, between the at least one first electrode and the one of at least one reference electrode and a counterelectrode, in response to the at least one of applying and setting an electric voltage between the at least one first electrode and the at least one reference electrode due to a chemical reaction proceeding at the at least one first electrode, the concentration of the at least one gas component in the gas mixture being determinable from the electric current;

wherein the measuring of the electric current between the at least one first electrode and the counterelectrode is performed at least intermittently within the recurring time intervals.

14. The method of claim 13, wherein the recurring time intervals recur periodically and have a length of 1 ms to 100 ms, and pause intervals of 1 ms to 100 ms lie between the recurring time intervals.

15. The method of claim 13, wherein at the at least one first electrode, the at least one gas component includes nitrogen oxide to be analyzed, and reacts to form oxygen and nitrogen, the oxygen thus formed being removable through the first solid electrolyte via the electric voltage at least one of applied and set during the recurring time intervals.

16. The method of claim 13, wherein a length of the recurring time intervals is selected so that the electric current between the at least one first electrode and the at least one reference electrode, measurable during the recurring time intervals as a function of time, is greater than a limiting current measurable at a constant electric voltage at a corresponding time.

* * * * *